United States Patent
Margulies et al.

[11] Patent Number: 6,086,590
[45] Date of Patent: Jul. 11, 2000

[54] CABLE CONNECTOR FOR ORTHOPAEDIC ROD

[75] Inventors: Joseph Y. Margulies, Armonk, N.Y.; Matthew N. Songer, Marquette; Francis J. Korhonen, Neqaunee, both of Mich.

[73] Assignee: Pioneer Laboratories, Inc., Marquette, Mich.

[21] Appl. No.: 09/241,980

[22] Filed: Feb. 2, 1999

[51] Int. Cl.[7] .................................................. A61B 17/58
[52] U.S. Cl. .............................................. 606/61; 606/74
[58] Field of Search .................. 606/74, 72, 73, 606/61

[56] References Cited

U.S. PATENT DOCUMENTS 5,380,326   1/1995   Lin ............................................ 606/61

*Primary Examiner*—Michael Buiz
*Assistant Examiner*—Julian W. Woo
*Attorney, Agent, or Firm*—George H. Gerstman; Garrettson Ellis

[57] ABSTRACT

A connector for securing surgical cable or wire to an implantable surgical rod or the like. The connector comprises a connector body having an open space for receiving the surgical rod or similar support device. The body carries a lock member for firmly affixing the connector and the rod together in a desired position along the rod. Typically, the lock member is a set screw. The connector also has a retention member carried on the connector in a rotatable manner. The retention member, typically in ring form, defines at least one bore extending there through for receiving the cable or wire, and retaining it in a desired position relative to the rod. Thus, tension can be placed upon broken bones or the like from a desired, controllable direction and with a desired magnitude of tension.

24 Claims, 3 Drawing Sheets

CABLE CONNECTOR FOR ORTHOPAEDIC ROD

BACKGROUND OF THE INVENTION

Orthopaedic rods are commonly used to support the spine where necessary in orthopaedic surgery as one major use. Surgical wire and cable is then wrapped around the adjacent bones that need extra support, the wire or cable then being wrapped around the orthopaedic rod.

In the prior art, there is a problem of controlling cable or wire directions in its attachment to the orthopaedic rod. Conventionally, one can gain directional control with a pedicle screw, and to a certain extent with a hook claw. However, a hook claw can give control in one direction only, namely the direction of its blade. Thus, in the prior art, there are problems during and after surgery in that control of the wire orientation is somewhat limited.

By this invention, surgical cable or wire can be connected to a surgical rod in a way that will allow pulling or pushing, as well as solid cranial-caudal axial and rotational control in a manner that is significantly improved over the prior art.

DESCRIPTION OF THE INVENTION

By this invention, a connector is provided for securing surgical cable or wire to an implantable surgical rod or other patient-implantable device. The connector comprises a connector body typically having an open space for receiving an orthopaedic rod. This space may be an aperture, or a recess which is open at the side defined by what is commonly called a hook. The connector body carries a lock member such as a set screw for firmly affixing the connector and the rod together in a desired position along the rod.

The connector also has a retention member which is carried on the connector in a rotatable manner. The retention member defines at least one bore which extends therethrough for receiving the cable or wire which is to be attached to the surgical rod, and retaining such cable or wire in a desired position relative to the rod, and also to the bones which the surgical cable or wire is provided to secure.

Typically, the retention member is a rotatable ring having a bore extending through it to receive the cable and wire as described above. A plurality of such bores may be provided, for example two, as shown in the specific embodiment.

When the locking member is a set screw, as shown in the specific embodiment, the set screw may define an outer head having an outwardly extending retention flange. Thus, the retention member may comprise a rotatable ring which is rotatably positioned and held about the set screw between the connector body and the retention flange.

When cable is being implanted around bone and being secured to an implantable rod, the connector may be moved along the rod to a desired position where the direction of tension of the cable is optimum for the situation in question. Then, the connector may be firmly attached to the rod by tightening of the set screw. The retention member will spontaneously rotate to the appropriate position, eliminating any possibility of cable loosening or slippage along the implantable rod, and reducing cable stress or kinking. The connector is firmly held by the reliable action of a set screw or other similar lock member for firmly affixing the connector and rod together in the desired position.

It thus becomes possible to compress or distract bone portions as the surgeon may desire by the following method: One places a surgical rod in the patient, and also places wire or cable around the bone portions which are to be compressed or distracted. One then tightens the wire or cable into a retained, tight position including at least one of: (1) sliding the connector along the surgical rod and (2) rotating the wire or cable engaging said connector, to position the wire or cable to compress, distract, or rotate the bone portions in a desired manner. One then tightly secures the connector to the surgical rod.

By this technique and through the connector of this invention, the surgeon is provided with significant new options for improved surgical performance with less difficulty, less need for pedicle screws, and less expense.

More broadly, this invention relates to a connector for securing surgical cable or wire (or ribbon, which is intended to be included in the definition of "surgical cable or wire"). The connector comprises a connector body having a fitment for receiving or connecting to a patient-implantable device in firmly locked manner. The patient-implantable device may be a surgical rod as specifically shown herein, but it may also comprise other implantable devices, for example, implantable prostheses for any joint, such as the hip or shoulder; for example, a prosthesis for total hip replacement. Also, the patient-implantable device may be a bone plate, with a connector of this invention providing cable or wire (or ribbon) connection to any of these patient-implantable devices for securing a bone, another implantable device, or the like to the patient-implantable implantable device, or for supporting the patient-implantable device in a desired position and retaining it with a cable or wire.

The connector of this invention also has a retention member comprising at least one of an aperture or a groove, for receiving the cable or wire and retaining it in a desired position relative to the implantable device. In the specific embodiments shown, this can accomplished by positioning the connector at a desired position along an implantable surgical rod. However, the same principle may be applied to other implantable devices as desired.

Thus, the cable or wire (or ribbon) can be connected to a patient-implantable device through the connector of this invention, which attaches to the patient-implantable device and can be adjustable in position with respect to the patient-implantable device, to provide improved flexibility for tubing or use.

In one disclosed embodiment, the retention member described above comprises an annular groove. In another disclosed embodiment, the retention member comprises a rotatable head having at least one aperture therein, as described above.

If desired, the connector of this invention may be directly attached to a patient-implantable device other than an rod (such as a bone plate) and may then be attached by cable to a hip or shoulder replacement prosthesis to assist in support and positioning particularly of the prosthesis, as may be desired by the surgeon. Alternatively, the connector of this invention may be carried on a bone plate or a hip or shoulder prosthesis, and may support and retain wires that are wrapped around a bone.

DESCRIPTION OF THE DRAWINGS

Referring to the drawings.

DESCRIPTION OF SPECIFIC EMBODIMENTS

Figure 1:
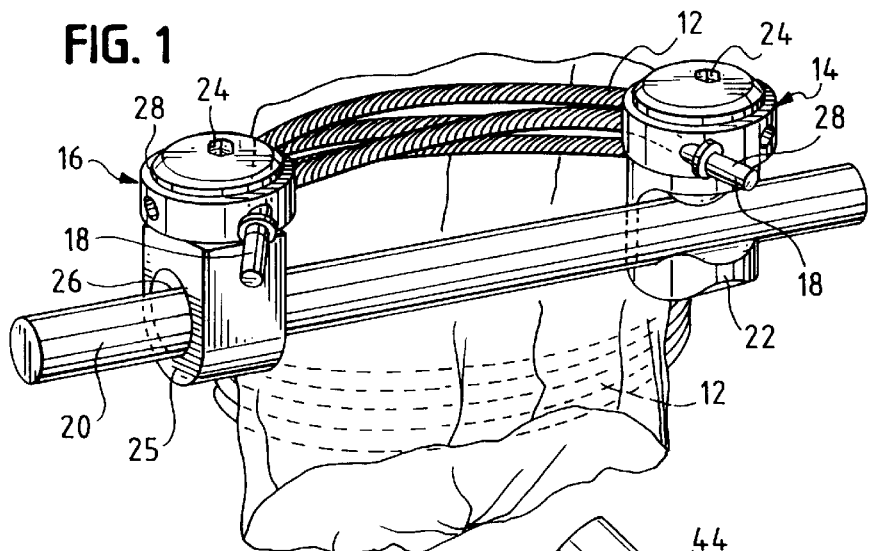
FIG. 1 is a perspective view of a bone broken into fragments and having two connectors in accordance with this invention, shown to be holding cable wrapped around the bone and retaining it in a desired tension and a desired direction of the tension, especially adjacent to the cable ends.

Referring to FIG. 1, a broken, multipiece bone 10 is shown to be secured together with several windings of surgical cable 12, which surround the broken bone. At the respective ends of wound surgical cable 12, the cable end portions extend through respective connectors 14 and 16 by extending through certain apertures thereof (to be described below) being secured in said apertures by respective crimps 18 of the known "top hat" type.

The respective connectors 14 and 16 are positioned along an implantable surgical rod 20. Connector 14 carries a hook 22 of known design which half surrounds surgical rod 20. Connector 14 is secured in position by a set screw 24, as shown in greater detail below.

Connector 16 has a body 25 which defines an aperture 26, through which rod 20 extends so that rod 20 is completely surrounded by connector body 25. Here also, a set screw 24 is used to secure connector 16 to rod 20.

Since the respective connectors 14 and 16 may slide along rod 20 to essentially any desired position as determined by the surgeon, it becomes possible to provide tension on the cable from a variety of directions in a manner substantially easier than in the prior art. The respective connectors 14, 16 are positioned as desired by the surgeon. Then, the loops of cable 12 may be tensioned in a conventional manner with a known tensioner, and the crimps 18 may be applied, to consequently apply a desired tension to the wound cable from desired directions depending on the positioning of the respective connectors 14, 16 along rod 20. Connectors 14, 16 are secured to rod 20 at any time desired by tightening of each respective set screw 24, for solid securance between each connector 14, 16 and surgical rod 20, with the consequence that the respective ends of cable 12 are solidly secured to surgical rod 20 as well.

In this embodiment, the respective connectors 14, 16 each carry a retention member 28 in ring form, of a design disclosed more specifically below. The ringlike retention member 28 can freely rotate, so that during the step of tensioning of cable 12, they rotate to the optimum position, assuring that no subsequent slippage of the cable can take place after tensioning, at least at the site of connection of the cable and connectors 14, 16.

Figure 2:
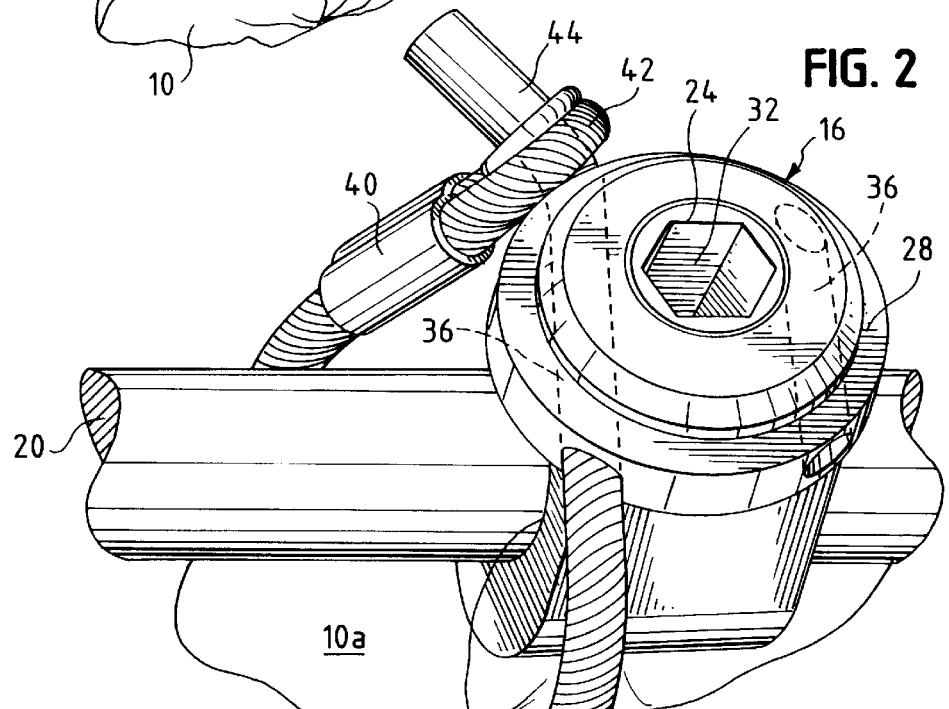
FIG. 2 is an enlarged, perspective view of another surgical situation, showing a single connector of this invention to be holding both ends of a cable which wraps a bone in a desired tension and direction of tension.
Figure 3:
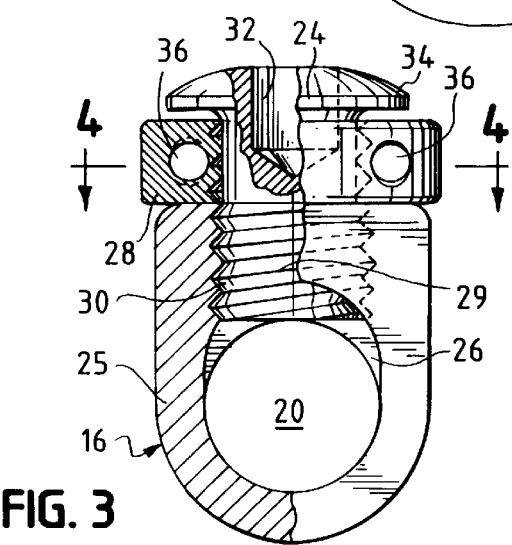
FIG. 3 is an elevational view, taken partly in section, showing the FIG. 2 embodiment of the connector of this invention.
Figure 4:
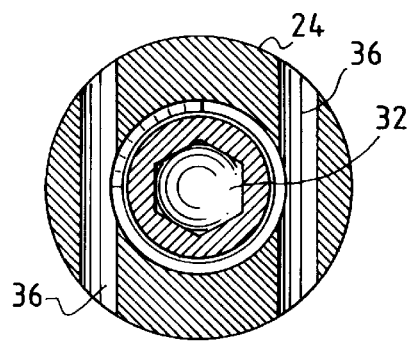
FIG. 4 is a sectional view taken along line 4—4 of FIG. 3.

Referring to FIGS. 2–4, connector member 16 is again specifically shown, carried on implantable surgical rod 20, which is positioned adjacent to another bone 10a. The design of connector 16 is identical in both FIGS. 1 and 2, and similar to the design of connector 14 except for the single difference of the C-shaped hook 22 in the case of connector 14, rather than the fully enclosed aperture 26 as is found in connector 16. Connector 16 is shown to have connector body 25, defining the complete aperture 26 discussed above, which surrounds and retains implantable surgical rod 20.

Body 25 carries lock member 24, specifically a set screw, for firmly affixing connector 16 and rod 20 together in a desired position along the rod. Such set screws are conventional, having threads 30 which engage corresponding threads of body 25 as particularly shown in FIG. 3, so that the set screw 24 may firmly and forcefully press against rod 20 when it is desired to secure connector 16 in place. Set screw 24 also carries, in this particular embodiment, a hexagonal hole 32 into which the tip of an Allen wrench can fit, to conventionally advance the set screw into securing relation with rod 20.

Set screw 24 carries an outer head which defines an outwardly extending retention flange 34, which in this embodiment extends 360 degrees around the set screw, but other types of flanges can also be suitable. One purpose of retention flange 34 is to retain the ring-like retention member 28, which is carried on connector 16 (and connector 14) in a rotatable manner as particularly shown in FIG. 3. Ring-like retention member 28 can rotate around set screw 24, being retained on one side by connector body 25 and on the other side by flange 34.

Retention ring 28 is shown to define a pair of holes 36, which extend completely through retention ring 28 to provide retentive access for cable 12a.

Accordingly, as particularly shown in FIG. 2, cable 12a may pass around bone 10a as desired by the surgeon for the best retention thereof. Cable 12a may also pass through one of holes 36 of connector 16. One end of cable 12a may be secured into a loop, being held by a conventional crimp 40, with the loop 42 surrounding another length of cable 12a which is secured by a conventional top-hat crimp 44, or other crimp as may be desired. Before crimp 44 is crimped into its retaining configuration, a conventional tensioner may be used to obtain the desired tension, following which crimp 44 is crushed with a conventional crimper, and any remaining cable projecting from the outer end of crimp 44 may be cut away.

Thus, the direction of cable tension against bone 10a may be controlled by the desired positioning of connector 16 on rod 20. When the desired positioning is achieved, set screw 24 may be tightened using hexagonal aperture 32 and an Allen wrench. The magnitude of the tension on cable 12a may be controlled in the conventional manner using a tensioner.

Thus, both the direction and the magnitude of tension on bone 10a applied by cable 12a can be more precisely controlled than in the prior art, with greater ease, speed, and reduced expense.

Referring to FIGS. 5 through 8, another embodiment of connector 50 for securing surgical cable is shown. Connectors 50 each have a connector body and an aperture, as in the previous embodiment, through which an implanted surgical rod 52 extends. A set screw 54 having a hexagonal socket for receiving an appropriate wrench may be used to secure by tightening the connector 50 to implantable rod 52. Thus, as in the previous embodiment, connector 50 can slide up and down the implantable rod 52 to a desired position which can be determined during the surgery. Then, when the desired position is reached, set screw 54 may be tightened to permanently secure connector 50 into the desired position.

Figure 6:
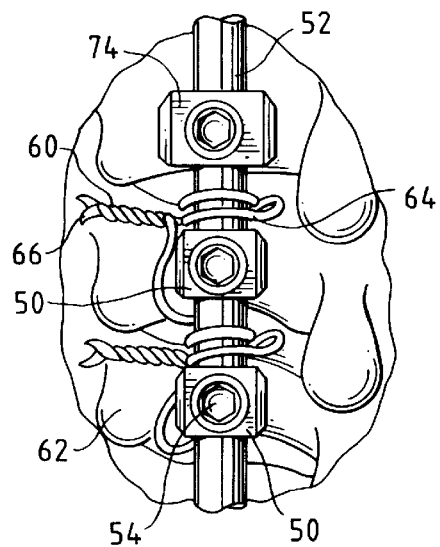
FIG. 6 is an enlarged view of a portion of FIG. 5.
Figure 5:
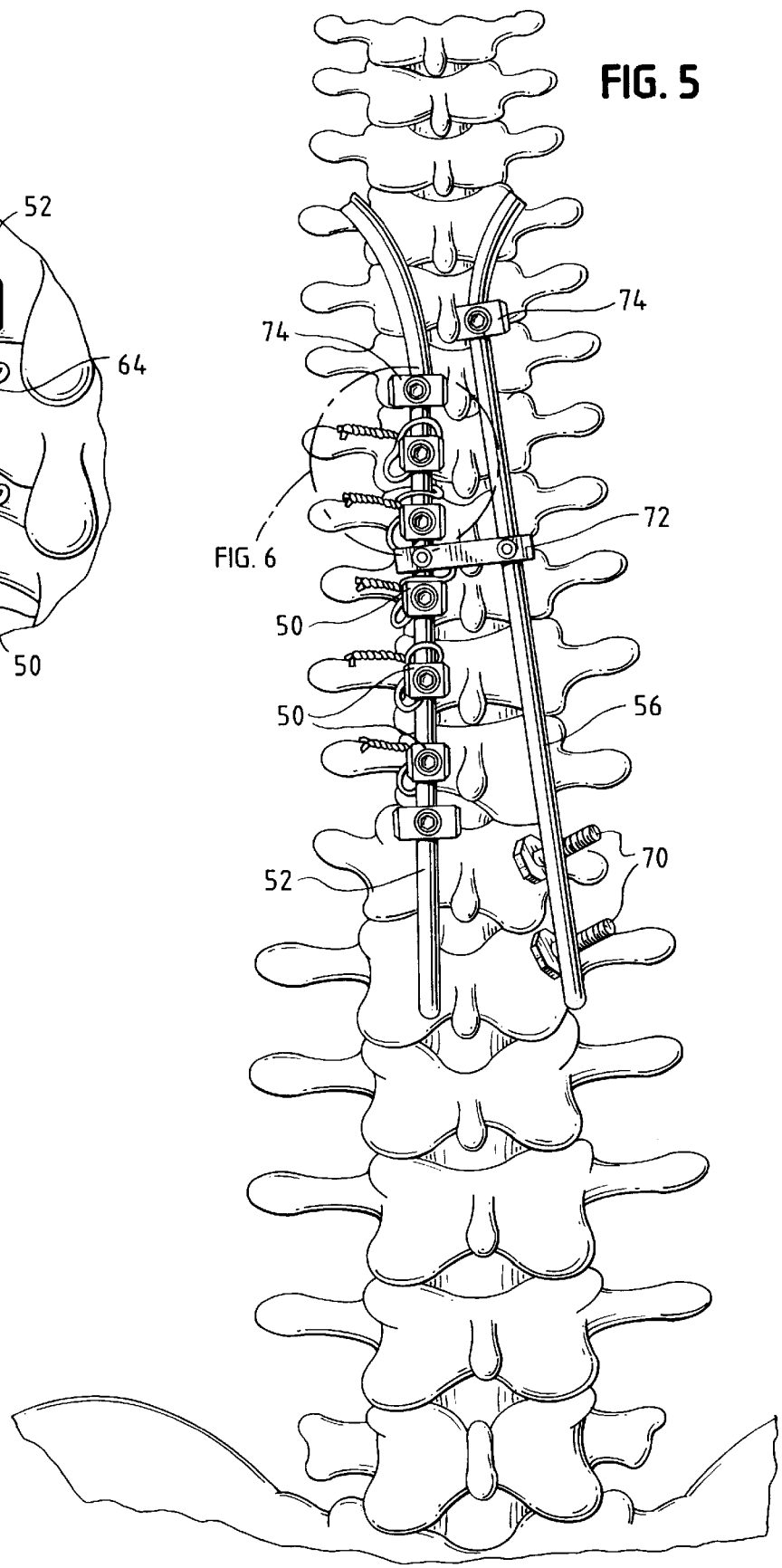
FIG. 5 is an elevational view of the spine of a patient, showing how an implantable array of rods and connectors in accordance with this invention can be implanted on the spine to provide cable or wire retention sites.
Figure 8:
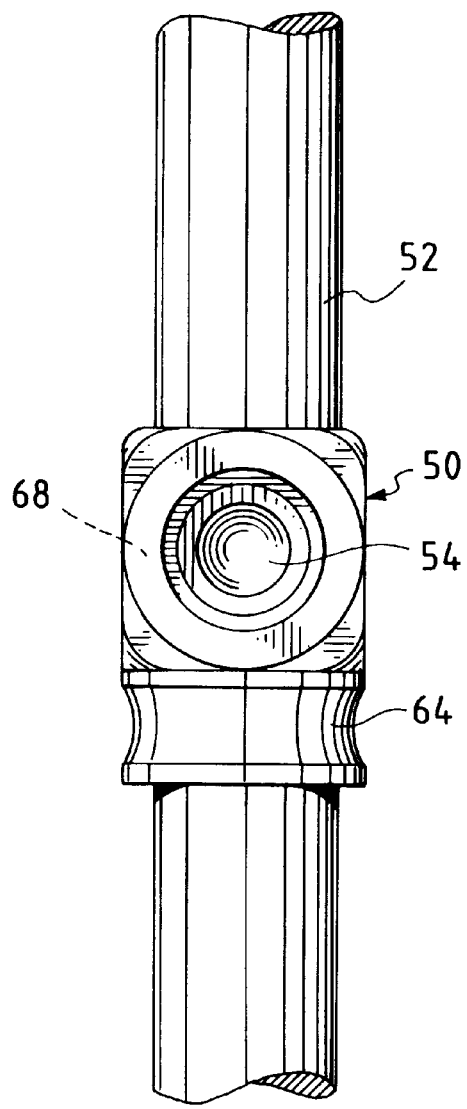
FIG. 8 is an elevational view, rotated 90° about the axis of the rod, showing the implantable connector of FIG. 7.
Figure 7:
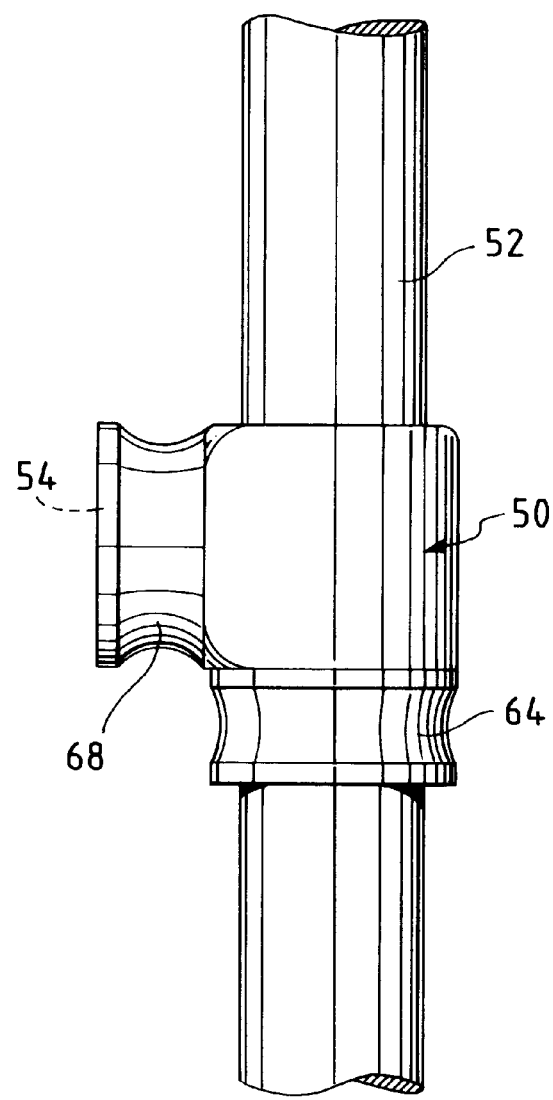
FIG. 7 is a further enlarged but inverted view of an implantable rod, showing one embodiment of the connector of this invention as an elevational view.

As particularly shown in FIGS. 5 and 6, surgical rod 52, and companion surgical rod 56, may be emplaced along the spine 58 of a patient. Various wires 60 may be attached, being wrapped around vertebra 62, (FIG. 6) with a portion of each wire resting in a portion of annular groove 64 in connector 50 for retention of the wire, which is formed into a loop with a twisted end 66. Thus, wire 60 is held in a desired position relative to the bone, and may be pulled in any of a variety of directions depending upon the desired positioning of its connector 50 on rod 52.

It can be seen that connectors 50 also carry a second annular groove 68 (FIG. 7) which occupies a plane perpendicular to annular groove 64, with groove 68 surrounding set screw 54. If and as desired, a cable or wire can be emplaced in annular groove 68 as well as, or as a replacement for, the emplacement of such a wire in annular groove 64. This can be done at the discretion of the surgeon, and gives him a wider range or choices and directions for the securance of surgical wire or cable between connector 50 and a bone or another patient-implantable device as described above.

The connectors of this invention may be made of any desirable material, particularly surgically implantable metals of types which are known and reliable for permanent implantation use.

Other conventional connectors such as screw posts 70 and screw connectors 72, 74 may be used to emplace the respective implantable rods 52, 56 during the surgical procedure. The patient is then closed up for convalescence, with the connectors of this invention reliably holding the wire or cable, in turn, while retaining bone or another surgical implantable device under tension from a desired direction, which is controllable depending upon the position of the connector of this invention on rod 20 or 52, for greater flexibility of choice on the part of the surgeon, leading to better clinical outcome.

The above has been offered for illustrative purposes only, it is not intended to limit the scope of the invention of this application, which is as defined in the claims below.

We claim:

1. A connector for securing surgical cable or wire to an implantable surgical rod, which connector comprises:

A connector body having an open space for receiving a surgical rod, said body carrying a lock member for firmly affixing the connector and the rod together in a desired position along the rod, said connector also having a retention member carried on said connector in a rotatable manner, said retention member defining at least one bore extending therethrough for receiving said cable or wire, and retaining it in a desired position relative to said rod.

2. The connector of claim 1 in which said retention member is a rotatable ring.

3. The connector of claim 1 in which said open space is a hole extending through said connector body.

4. The connector of claim 1 in which said open space is a recess partially surrounded by a hook member of said body.

5. The connector of claim 1 in which said rotatable member defines a plurality of spaced bores for receiving said cable or wire.

6. The connector of claim 1 in which the lock member is a set screw.

7. The connector of claim 6 in which the set screw defines an outer head having an outwardly extending retention flange, said retention member comprising a rotatable ring positioned about said set screw between said connector body and the retention flange.

8. A connector for securing a surgical cable or wire to an implantable surgical rod, which connector comprises a connector body having an open space for receiving an orthopaedic rod, said body carrying a set screw for firmly affixing the connector and the rod together in a desired position along the rod, said connector also having a rotatable retention ring carried on said connector in a rotatable manner, said retention ring defining at least one bore extending therethrough for receiving said cable or wire, and retaining it in a desired position relative to said rod.

9. The connector of claim 8 in which said at least one bore extends in a direction transverse to the axis of the orthopaedic rod when the connector is secured thereto.

10. The connector of claim 8 in which said rotatable retention ring defines a plurality of spaced bores for receiving said cable or wire.

11. The connector of claim 10 in which said set screw defines an outer head having an outwardly extending retention flange, said rotatable retention ring being positioned about said set screw between the connector body and the retention flange.

12. The connector of claim 11 in which said open space is a hole extending through said connector body.

13. The connector of claim 12 in said open space is partially surrounded by a hook member of said body.

14. The surgical method of compressing or distracting bone portions, which comprises:

emplacing a surgical rod in a patient; placing wire or cable around said bone portions; placing a connector into engagement with said rod and with said wire or cable; tightening said wire or cable into a retained position with said bone and said connector including the step of at least one of: (1) sliding said connector along said surgical rod and (2) rotating the wire or cable engaging said connector to position said wire or cable to compress, distract, or rotate said bone portions in a desired manner; tightly securing said connector to the surgical rod; and tightly securing said wire or cable to the connector.

15. The method of claim 14 in which said wire or cable is secured to a rotatable portion of said connector.

16. A connector for securing surgical cable or wire to an implantable surgical support device, which connector comprises: a connector body configured for being secured to said implantable support device, said body carrying a lock for firmly affixing the connector and the implantable support device together in an adjustably selected position with respect to the support device, said connector also having a retention member carried on the connector for receiving said cable or wire and retaining it in a desired position relative to said implantable support device.

17. A connector for securing surgical cable or wire which connector comprises:

a connector body having a fitment for connecting to a patient-implantable device in firmly locked manner, said connector body also having a retention member comprising at least one of an aperture or a groove for receiving said cable or wire and retaining it in a desired position relative to said patient implantable device.

18. The connector of claim 17 in which said retention member comprises an annular groove.

19. The connector of claim 18 in which said retention member comprises a first annular groove, plus a second annular groove positioned transversely of the first annular groove.

20. The connector of claim 17 in which said patient-implantable device is a rod.

21. The connector of claim 17 in which the patient-implantable device is a prosthesis for a joint.

22. The connector of claim 17 in which said cable or wire is for securing a bone to said connector.

23. The connector of claim 17 in which said cable or wire is for securing a patient-implantable device to said connector.

24. The connector of claim 17 in which said retention member is carried on said connector in rotatable manner and defines at least one bore extending therethrough for receiving said cable or wire and retaining it in said desired position.

* * * * *